United States Patent
Mankura et al.

(10) Patent No.: US 10,189,770 B2
(45) Date of Patent: Jan. 29, 2019

(54) PRODUCTION METHOD OF HIGHLY UNSATURATED FATTY ACID ETHYL ESTER

(71) Applicant: Bizen Chemical Co., Ltd., Akaiwa-shi, Okayama (JP)

(72) Inventors: Mitsumasa Mankura, Akaiwa (JP); Yoshihisa Misawa, Akaiwa (JP); Yoshio Shimizu, Akaiwa (JP)

(73) Assignee: Bizen Chemical Co., Ltd., Akaiwa-shi, Okayama (JP)

( * ) Notice: Subject to any disclaimer, the term of this patent is extended or adjusted under 35 U.S.C. 154(b) by 0 days.

(21) Appl. No.: 15/577,726

(22) PCT Filed: May 30, 2016

(86) PCT No.: PCT/JP2016/002613
§ 371 (c)(1),
(2) Date: Nov. 28, 2017

(87) PCT Pub. No.: WO2016/194360
PCT Pub. Date: Dec. 8, 2016

(65) Prior Publication Data
US 2018/0155268 A1    Jun. 7, 2018

(30) Foreign Application Priority Data
Jun. 1, 2015   (JP) ................................ 2015-111793

(51) Int. Cl.
| | |
|---|---|
| C07C 67/62 | (2006.01) |
| B01D 15/00 | (2006.01) |
| B01J 20/10 | (2006.01) |
| B01J 20/12 | (2006.01) |
| B01J 20/20 | (2006.01) |
| C07C 67/58 | (2006.01) |
| C07C 67/60 | (2006.01) |
| C07C 69/533 | (2006.01) |
| C07C 69/58 | (2006.01) |
| B01D 15/08 | (2006.01) |
| C11B 3/00 | (2006.01) |

(52) U.S. Cl.
CPC .............. C07C 67/62 (2013.01); B01D 15/00 (2013.01); B01D 15/08 (2013.01); B01J 20/10 (2013.01); B01J 20/12 (2013.01); B01J 20/20 (2013.01); C07C 67/58 (2013.01); C07C 67/60 (2013.01); C07C 69/533 (2013.01); C07C 69/58 (2013.01); C11B 3/00 (2013.01)

(58) Field of Classification Search
CPC ... C07C 67/62; C11B 3/06; C11B 3/10; C11B 3/001; B01J 20/10; B01J 20/12; B01D 15/00; B01D 15/08
See application file for complete search history.

(56) References Cited

U.S. PATENT DOCUMENTS

| | | | |
|---|---|---|---|
| 5,006,281 A * | 4/1991 | Rubin | A23D 9/00 424/522 |
| 5,189,189 A | 2/1993 | Misawa et al. | |
| 5,571,935 A | 11/1996 | Sekula et al. | |
| 2011/0224452 A1 * | 9/2011 | Sakaguchi | C07C 67/58 554/191 |
| 2016/0208296 A1 * | 7/2016 | Shimizu | C11B 1/025 |

FOREIGN PATENT DOCUMENTS

| | | | | |
|---|---|---|---|---|
| CN | 102994236 A * | 3/2013 | ............... | C11C 1/08 |
| JP | 8-38050 A | 2/1996 | | |
| JP | 08-100191 A | 4/1996 | | |
| JP | 2786748 B2 | 8/1998 | | |
| JP | 2895258 B2 | 5/1999 | | |
| JP | 2935555 B2 | 8/1999 | | |
| JP | 3001954 B2 | 1/2000 | | |
| JP | 2010-64974 A | 3/2010 | | |
| JP | 5503856 B2 | 5/2014 | | |
| WO | WO 2015/029364 A1 * | 3/2015 | ............... | C11C 3/10 |

OTHER PUBLICATIONS

JP H08-100191, Yokoyama Haruhiko et al., Purification of Highly unsaturated fattu acod pr ester thereof, English translation, 13 pages (Year: 1996).*
CN 102994236, Zhang Yong, et al., Method for preparing fatty acid ethyl ester with omega-3 content of more than 90 percent, , English Translation, 16 pages (Year: 2013).*

* cited by examiner

Primary Examiner — Yate' K Cutliff
(74) Attorney, Agent, or Firm — Seed IP Law Group LLP

(57) ABSTRACT

The present invention provides a method of producing/purifying highly unsaturated fatty acids and/or derivatives thereof while suppressing deterioration of a silver salt aqueous solution, in production/purification of highly unsaturated fatty acids and/or derivatives thereof using the aqueous solution of silver salt. The present invention also contacts or mixes a mixture having a peroxide value (POV) of 10 or smaller with an aqueous solution of silver salt, in a method of purifying highly unsaturated fatty acids and/or derivatives thereof from a mixture comprising highly unsaturated fatty acids and/or derivatives thereof.

8 Claims, No Drawings

PRODUCTION METHOD OF HIGHLY UNSATURATED FATTY ACID ETHYL ESTER

TECHNICAL FIELD

The present invention relates to a novel production method of a highly unsaturated fatty acid ethyl ester. In addition, the present invention relates to a purification method of a highly unsaturated fatty acid ethyl ester.

BACKGROUND ART

Highly unsaturated fatty acid is a collective term of fatty acids having many double bonds. Attention has been paid to the biological functions of highly unsaturated fatty acids and derivatives thereof, especially icosapentaenoic acid and docosapentaenoic acid derived from fish oils. The demand thereof has been increasing, including high-purity icosapentaenoic acid as a pharmaceutical. Thus, there is a demand for a novel production method of a highly unsaturated fatty acid ethyl ester, or novel purification method of a highly unsaturated fatty acid ethyl ester, that is more simple and economic, and that could achieve higher purity and/or higher yield.

A silver complex method, which utilizes the characteristic of highly unsaturated fatty acids and derivatives thereof that they form a complex with silver ions and become water-soluble, is known as one of purification methods of highly unsaturated fatty acids (Patent Literatures 1-4). Patent Literatures 1-4 describe that silver salt that is used for purification of highly unsaturated fatty acids and derivatives thereof can be reutilized. However, silver salt has a property of being extremely liable to deterioration. When highly unsaturated fatty acids and derivatives thereof are purified by using deteriorated silver salt, contamination of impurities and deterioration of flavor would occur, and it is not possible to obtain good purified products. Accordingly, reutilization of silver salt is extremely difficult in reality, and when purifying highly unsaturated fatty acids and derivatives thereof on an industrial scale, there is a problem that a new silver salt aqueous solution needs to be prepared each time, and the purification cost becomes extremely expensive.

In order to provide highly unsaturated fatty acids and derivatives thereof having a good quality level at a low cost, a method of allowing the free fatty acid content in a silver salt aqueous solution that will be reutilized to be below a predetermined value, was developed as a technique of enabling repeated reutilization of a silver salt aqueous solution for a long period of time (Patent Literature 5). This method is characterized in that a silver salt aqueous solution is made into contact with a free fatty acid reducing agent to manage the free fatty acid content in the silver salt aqueous solution to be 0.2 meq or smaller per 1 g of silver. However, as was made clear by the inventors and as will be described below, if only the acid value of raw materials is focused and attention is not paid to the peroxide value, the peroxides of the raw materials may cause silver nitrate deterioration in the silver nitrate aqueous solution, and may cause decrease in production yield and the like. As will be shown below, the inventors made clear that peroxides in raw materials cause silver nitrate deterioration in silver nitrate aqueous solutions and cause decrease in production yield and the like, and the inventors completed the present invention characterized in that the peroxide value in raw materials is defined to 10 or smaller to decrease silver nitrate deterioration. Although Patent Literature 5 describes an acid value regarding the quality of raw materials, it does not have descriptions concerning a peroxide value. An acid value, which is the quality index of raw materials, does not correlate with a peroxide value. Thus, the subject matter described in Patent Literature 5 may develop a problem that silver nitrate deterioration in a silver nitrate aqueous solution is caused by the peroxides of raw materials, and decrease in production yield and the like are caused.

CITATION LIST

Patent Literature

[PTL 1]
Japanese Patent No. 2786748
[PTL 2]
Japanese Patent No. 2895258
[PTL 3]
Japanese Patent No. 2935555
[PTL 4]
Japanese Patent No. 3001954
[PTL 5]
Japanese Patent No. 5503856

SUMMARY OF INVENTION

Technical Problem

The objective of the present invention is to, when purifying highly unsaturated fatty acid derivatives from a mixture (e.g., raw materials) comprising highly unsaturated fatty acid derivatives, decrease the peroxide value of the mixture to improve the yield and the like in purification/production of highly unsaturated fatty acid derivatives.

Solution to Problem

The inventors have discovered that the lipid peroxides of highly unsaturated fatty acid ethyl esters, which are raw materials, give a significant influence on deterioration of silver salt aqueous solutions, and completed the present invention. While not wishing to be bound by theory, the inventors inferred that decrease in the processing ability of a silver salt aqueous solution is caused because of the binding of a lipid peroxide and/or an oxidation product of the lipid peroxide and/or a degradation product of the lipid peroxide with the silver salt aqueous solution. Thus, the inventors considered that it is important to remove such lipid peroxide and/or oxidation product of the lipid peroxide and/or degradation product of the lipid peroxide in raw materials, and discovered that deterioration of a silver salt aqueous solution (e.g., silver nitrate) can be suppressed by decreasing the peroxide value of a highly unsaturated fatty acid ethyl ester, which is the raw material, or by providing a raw material of highly unsaturated fatty acid ethyl ester having a low peroxide value, thereby completing the novel production method/novel purification method of the present invention.

In the present invention, for example, by reducing the peroxide value of a highly unsaturated fatty acid ethyl ester, which is the raw material, or by providing a raw material of highly unsaturated fatty acid ethyl ester having a low peroxide value, and contacting such raw material of highly unsaturated fatty acid ethyl ester with a silver salt aqueous solution, production/purification of highly unsaturated fatty acids and/or derivatives thereof is enabled while suppressing deterioration of the silver salt aqueous solution.

The present invention provides, for example, the following:

(Item 1)

A method of purifying highly unsaturated fatty acid derivatives from a mixture comprising highly unsaturated fatty acid derivatives, the method comprising (b) contacting the mixture with an aqueous solution of silver salt, wherein a peroxide value of the mixture is 10 or smaller.

(Item 2)

A method of purifying highly unsaturated fatty acid derivatives from a mixture comprising highly unsaturated fatty acid derivatives, the method comprising (b) mixing the mixture with an aqueous solution of silver salt, wherein a peroxide value of the mixture is 10 or smaller.

(Item 3)

A method of purifying highly unsaturated fatty acid derivatives from a mixture comprising highly unsaturated fatty acid derivatives, the method comprising (a) decreasing a peroxide value of the mixture to 10 or smaller; and (b) contacting the mixture with an aqueous solution of silver salt.

(Item 4)

A method of purifying highly unsaturated fatty acid derivatives from a mixture comprising highly unsaturated fatty acid derivatives, the method comprising (a) decreasing a peroxide value of the mixture to 10 or smaller; and (b) mixing the mixture with an aqueous solution of silver salt.

(Item 5)

The method according to any of items 1-4, wherein the highly unsaturated fatty acid derivatives are highly unsaturated fatty acid ethyl esters.

(Item 6)

The method according to item 5, wherein the highly unsaturated fatty acid ethyl esters are selected from the group consisting of 18:3ω3, 18:3ω6, 18:4ω3, 20:4ω6, 20:5ω3, 22:5ω3, and 22:6ω3.

(Item 7)

The method according to any of items 1-4, wherein the aqueous solution of silver salt is a silver nitrate aqueous solution.

(Item 8)

The method according to item 3 or 4, wherein the step (a) comprises contacting the mixture with a POV reducing agent selected from the group consisting of acid clay, activated clay, activated carbon, and silicic acid.

(Item 9)

The method according to any of items 1-4, further comprising (c) adding an antioxidant to the mixture.

(Item 10)

The method according to item 9, wherein the step (c) is performed before the step (b).

(Item 11)

The method according to any of items 1-4, wherein the step (b) is performed under a condition selected from the group consisting of under a nitrogen gas environment and under a light-blocking environment.

(Item 12)

A method of purifying highly unsaturated fatty acid derivatives from a mixture comprising highly unsaturated fatty acid derivatives, comprising (b) contacting the mixture with an aqueous solution of silver salt, wherein the method is characterized in that a peroxide value of the mixture is managed to 10 or smaller by contacting the mixture with a POV reducing agent.

(Item 13)

A method of purifying highly unsaturated fatty acid derivatives from a mixture comprising highly unsaturated fatty acid derivatives, the method comprising (b) mixing the mixture with an aqueous solution of silver salt, wherein the method is characterized in that a peroxide value of the mixture is managed to 10 or smaller by mixing the mixture with a POV reducing agent.

(Item 14)

The method according to item 12 or 13, wherein the highly unsaturated fatty acid derivatives are highly unsaturated fatty acid ethyl esters.

(Item 15)

The method according to item 14, wherein the highly unsaturated fatty acid ethyl esters are selected from the group consisting of 18:3ω3, 18:3ω6, 18:4ω3, 20:4ω6, 20:5ω3, 22:5ω3, and 22:6ω3.

(Item 16)

The method according to item 12 or 13, wherein the aqueous solution of silver salt is a silver nitrate aqueous solution.

(Item 17)

The method according to item 12 or 13, wherein the POV reducing agent is selected from the group consisting of acid clay, activated clay, activated carbon, and silicic acid.

(Item 18)

The method according to item 12 or 13, further comprising (c) adding an antioxidant to the mixture.

(Item 19)

The method according to item 18, wherein the step (c) is performed before the step (b).

(Item 20)

The method according to item 12 or 13, wherein the step (b) is performed under a condition selected from the group consisting of under a nitrogen gas environment and under a light-blocking environment.

Advantageous Effects of Invention

The present invention provides a method of producing/purifying highly unsaturated fatty acids and/or derivatives thereof while suppressing deterioration of a silver salt aqueous solution, in production/purification of highly unsaturated fatty acids and/or derivatives thereof using the aqueous solution of silver salt.

DESCRIPTION OF EMBODIMENTS

Hereinafter, the present invention will be described. Throughout the present specification, it should be understood that unless particularly stated otherwise, an expression in its singular form also includes the conception of plurality. It should be also understood that unless particularly stated otherwise, the terms used in the present specification have the meanings that are conventionally used in the art. Therefore, unless defined otherwise, all technical and scientific terms used in the present specification have the same meanings as commonly understood by those having ordinary skill in the art to which the present invention pertains. In the case of conflict, the present specification, including the definitions, will control. In addition, in the present specification, "wt %" and "percent concentration of mass" can be interchangeably used. Furthermore, in the present specification, unless particularly stated otherwise, "%" means "wt %".

Definition of Terms

Hereinafter, the definitions of the terms that are particularly used in the present specification will be listed.

The term "raw material oils and fats" as used herein refers to oils and fats that are used as the raw materials in the purification of the present invention. Deacidification treatment may or may not be performed on the raw material oils and fats. Preferably, the raw material oils and fats of the present invention are raw material oils and fats on which deacidification treatment is performed.

The term "purification" as used herein refers to any operation that increases the concentration of substances to be the target of purification.

The term "peroxide value" as used herein is interchangeably used with "POV", and it represents an amount of peroxides, which are the primary products generated in the early stage of autoxidation of oils and fats. While not wishing to be bound by theory, it is considered that deterioration of silver salt (e.g., silver nitrate) is caused due to the lipid peroxide included in the mixture (raw material oils and fats). In other words, it appears that silver salt such as silver nitrate is denatured due to the reaction of silver salt such as silver nitrate with lipid peroxide. In addition, when a peroxide exists in the mixture (raw material oils and fats), since the peroxide is unstable, it is degraded and generates aldehyde. Since aldehyde generally has toxicity, it is also important to suppress the generation of aldehyde. The POV of the mixture (e.g., raw material oils and fats) used in the purification method of the present invention is 14 or smaller, 13 or smaller, 12 or smaller, 11 or smaller, 10 or smaller, 9 or smaller, 8 or smaller, 7 or smaller, 6 or smaller, 5 or smaller, 4 or smaller, 3 or smaller, 2 or smaller, 1 or smaller, or 0.5 or smaller. The "peroxide value (POV)" can be measured by reacting potassium iodide with the sample, and titrating the free iodine from potassium iodide by hydroperoxide in the oils and fats. In more details, it is as described in "The JOCS Standard Methods for the Analysis of Fats, Oils and Related Materials", 2003 Edition (edited by Japan Oil Chemists' Society).

The term "acid value" as used herein is an index of carboxylic acids included in fatty acids, and it refers to the number of mg of potassium hydroxide that is required to neutralize the free fatty acids included in 1 g of the sample. The measurement method of the acid value is as described in "The JOCS Standard Methods for the Analysis of Fats, Oils and Related Materials" 2003 Edition (edited by Japan Oil Chemists' Society).

The "peroxide value" does not have a direct relationship with the "acid value". The value of the peroxide value gets higher as the oxidation advances, and peroxides are generated. However, since peroxides are unstable, they are degraded over time. In addition, even if the acid value of a mixture is low, the peroxide value (POV) might be high. For example, when a sample is contacted with a POV reducing agent the POV does not necessarily becomes 10 or smaller. Thus, in order to confirm that the POV is 10 or smaller, measurement of POV is necessary. Even if the acid value is 5 or smaller, the POV is not necessarily 10 or smaller, and rather, the POV often exceeds 10. In addition, in Patent Literature 5, sufficient results could not be obtained in prevention of deterioration of a silver salt aqueous solution by only setting the acid value to 5 or smaller. Thus, it was essential to set the free fatty acid content per 1 g of silver to 0.2 meq or smaller.

While not wishing to be bound by theory, in an aspect of the present invention, decrease of the processing ability of a silver salt aqueous solution is suppressed by removing a lipid peroxide and/or an oxidation product of the lipid peroxide and/or a degradation product of the lipid peroxide in the raw materials. The method of removing such lipid peroxide and/or an oxidation product of the lipid peroxide and/or a degradation product of the lipid peroxide in the raw materials representatively can be decrease of the peroxide value due to processing by a "POV reducing agent", but is not limited thereto. As long as such lipid peroxide and/or oxidation product of the lipid peroxide and/or degradation product of the lipid peroxide are removed from the raw materials, even if the peroxide value is not decreased, reduction in the processing ability of the silver salt aqueous solution can be suppressed, and it is possible to exert the desired effect of the present invention.

The term "POV reducing agent" as used herein refers to an agent that has action of decreasing the "peroxide value (POV)". For example, the POV reducing agent can be, but is not limited to, acid clay, activated clay, activated carbon, and silicic acid. As silicic acid (also referred to as silica), for example, silica gel, which is gelated silicic acid, can be utilized. In the present invention, for example, the method of allowing the peroxide value of a mixture comprising highly unsaturated fatty acid derivatives to be 10 or smaller can be, but is not limited to, contacting of the mixture with the "POV reducing agent", mixing of the mixture with the "POV reducing agent", input of the "POV reducing agent" into the mixture for stirring, or liquid-passing of the mixture through a column filled with the "POV reducing agent".

The term "highly unsaturated fatty acids" as used herein means unsaturated fatty acids having 16 or higher carbon number, which also have two or more double bonds within the molecule. For example, they can be, but are not limited to, docosahexaenoic acid (C22:6, DHA), eicosapentaenoic acid (C20:5, EPA), arachidonic acid (C20:4, AA), docosapentaenoic acid (C22:5, DPA), stearidonic acid (C18:4), linolenic acid (C18:3), and linoleic acid (C18:2). The derivatives of the highly unsaturated fatty acids that can be obtained with the acquisition method of the present invention refer to derivatives where fatty acids may or may not be the free type. For example, they can be, but are not limited to, highly unsaturated fatty acids, and ester-type derivatives such as methyl ester and ethyl ester, amide-type derivatives such as amide and methyl amide, fatty alcohol-type derivatives, triglyceride, diglyceride, and monoglyceride, of highly unsaturated fatty acids.

The term "silver salt" as used herein refers to silver salt that may form a complex with unsaturated bonds in unsaturated fatty acids. For example, it can be, but is not limited to, silver nitrate, silver perchlorate, silver acetate, silver trichloroacetate, and silver trifluoroacetate. The silver salt is dissolved into water such that the concentration becomes, preferably 15% or higher, more preferably 20% or higher, and even more preferably 40% or higher, to achieve a silver salt aqueous solution, and this is used for purification of highly unsaturated fatty acid derivatives. In addition, the silver salt concentration in the silver salt aqueous solution is not particularly limited, but preferably the saturating concentration is the upper limit.

The term "antioxidant" as used herein refers to a substance that reduces or removes harmful reactions involved with oxygen in living organisms, foods, daily necessities, and industrial raw materials. Representatively, the antioxidant can be, but is not limited to, butylhydroxytoluene, tocopherol, and a tocopherol derivative. For example, the tocopherol derivative can be, but is not limited to, d-α-tocopherol, d-β-tocopherol, d-γ-tocopherol, d-δ-tocopherol, 1-α-tocopherol, 1-β-tocopherol, 1-γ-tocopherol, and 1-δ-tocopherol; dl-α-tocopherol, dl-β-tocopherol, dl-γ-tocopherol, and dl-δ-tocopherol, which are mixtures thereof; and tocopherol acetate, tocopherol succinate, tocopherol phosphate, tocopherol aspartate, tocopherol glutamate, tocopherol palmitate, tocopherol nicotinate, tocopherol linoleate, and polyethoxylated tocopherol, which are derivatives thereof.

In the purification method of the present invention, the method of selectively separating highly unsaturated fatty acid derivatives from a mixture of derivatives of fatty acids is representatively performed by, but is not limited to: adding an aqueous solution of silver salt that may forma complex with unsaturated bonds into the above-described mixture of derivatives of fatty acids containing the highly unsaturated fatty acid derivatives; stirring preferably for 5 minutes to 4 hours, more preferably for 10 minutes to 2 hours to form the complex of water-soluble silver salt-highly unsaturated fatty acid derivatives; and selectively dissolving only the highly unsaturated fatty acid derivatives into a silver salt aqueous solution.

In addition, with regard to the reaction temperature of the above-described highly unsaturated fatty acid derivatives and the silver salt aqueous solution, the lower limit can be any temperature as long as the silver salt aqueous solution is a liquid, and the upper limit is 100° C. However, in consideration of the oxidative stability of the highly unsaturated fatty acid derivatives, the solubility of silver salt to water, the generation speed of the complex, and the like, the reaction temperature is preferably 10 to 30° C.

At the time of contacting the above-described highly unsaturated fatty acid derivatives with the silver salt aqueous solution, said contact is preferably performed under inert gas, e.g., nitrogen atmosphere, while blocking out light by considering the oxidative stability of the highly unsaturated fatty acid derivatives and the stability of silver salt. For example, by setting nitrogen atmosphere during production, incorporation of oxygen, which is the cause of oxidation, can be blocked, and it is also possible to suppress the increase of peroxides due to oxidation of raw materials. In addition, by blocking out the light, which promotes oxidation, it is possible to further suppress oxidation and suppress the increase of peroxides.

The method of dissociating the highly unsaturated fatty acid derivatives from the complex of the above-described highly unsaturated fatty acid derivatives and silver salt is not particularly limited, but it is for example, extraction by organic solvents and a method of adding water to insolubilize the highly unsaturated fatty acid derivatives for separation.

In the purification method/production method of highly unsaturated fatty acid derivatives using a mixture (raw materials) having a low peroxide value, which is the characteristic of the present invention, for example, it is possible to combine (1) management of the free fatty acid content in the mixture (raw materials) and/or (2) management of the acid value in the mixture (raw materials). For example, in an aspect of the present invention, the free fatty acid content in the silver salt aqueous solution is managed to 0.5 meq or smaller, 0.4 meq or smaller, 0.3 meq or smaller, 0.25 meq or smaller, 0.2 meq or smaller, 0.15 meq or smaller, 0.1 meq or smaller, or 0.07 meq or smaller. For example, in another aspect of the present invention, the acid value in the mixture (raw materials) can be managed to 10 or smaller, 9 or smaller, 8 or smaller, 7 or smaller, 6 or smaller, 5 or smaller, 4 or smaller, 3 or smaller, 2 or smaller, or 1 or smaller.

Hereinafter, the purification method of highly unsaturated fatty acid derivatives of the present invention will be explained more specifically based on the Examples and the like. However, the present invention is not limited thereto.

EXAMPLES

Example 1

A highly unsaturated fatty acid ethyl ester was purified from a fatty acid ethyl ester mixture by the following method.

Firstly, 50 g of distilled water was added to 50 g of silver nitrate to be stirred/dissolved. 20 g of a mixture of fatty acid ethyl esters (acid value 0.7; POV 6; EPA ethyl ester purity 44.9% (fatty acid composition area %); DHA ethyl ester purity 7.4%) was mixed with 100 g of this silver nitrate aqueous solution, and stirring was performed for 30 minutes at 20° C. Subsequently, the solution was left to stand for 30 minutes, and was separated into two layers. This upper layer was disposed, and only the lower layer was separately collected for addition of 100 g of cyclohexane to be stirred for 30 minutes at 60° C. Subsequently, the solution was left to stand for 30 minutes, and was separated into two layers. This upper layer was separately collected to obtain a concentrate of highly unsaturated fatty acid ethyl esters. In addition, the lower layer containing silver nitrate was separately taken to measure the free fatty acid content. This lower layer containing silver nitrate was used for purification of highly unsaturated fatty acid ethyl esters again. The above-described reactions were carried out under nitrogen atmosphere. These operations were repeated.

TABLE 1

(Summary of results of Example 1)

| Batch number | Fatty acid derivative | | | | Purified highly unsaturated fatty acid derivative | | | | |
| --- | --- | --- | --- | --- | --- | --- | --- | --- | --- |
| | peroxide value | acid value | EPA ethyl ester (%) | DHA ethyl ester (%) | peroxide value | acid value | yield (%) | EPA ethyl ester (%) | DHA ethyl ester (%) |
| 1 | 6.0 | 0.7 | 44.9 | 7.4 | 5.6 | 0.7 | 46.5 | 76.8 | 13.5 |
| 2 | | | | | 5.9 | 0.7 | 47.0 | 77.0 | 13.4 |
| 3 | | | | | 6.4 | 0.6 | 46.9 | 77.2 | 13.1 |
| 4 | | | | | 5.5 | 0.8 | 46.5 | 76.9 | 13.3 |
| 5 | | | | | 5.8 | 0.8 | 46.7 | 76.5 | 13.6 |
| 6 | | | | | 6.1 | 0.8 | 46.9 | 77.1 | 13.1 |
| 7 | | | | | 6.3 | 0.8 | 46.7 | 76.9 | 13.6 |

TABLE 1-continued (Summary of results of Example 1)

| | Fatty acid derivative | | | | Purified highly unsaturated fatty acid derivative | | | | |
|---|---|---|---|---|---|---|---|---|---|
| Batch number | peroxide value | acid value | EPA ethyl ester (%) | DHA ethyl ester (%) | peroxide value | acid value | yield (%) | EPA ethyl ester (%) | DHA ethyl ester (%) |
| 8 | | | | | 5.9 | 0.8 | 47.2 | 77.2 | 13.0 |
| 9 | | | | | 5.7 | 0.8 | 46.9 | 76.7 | 13.4 |
| 10 | | | | | 6.0 | 0.8 | 47.1 | 77.0 | 13.1 |

The results of treating 10 batches of the above-described mixture are shown in the above-described Table 1.

Example 2 (Using Raw Materials Having Various POVs and Acid Values)

A highly unsaturated fatty acid ethyl ester was obtained from a fatty acid ethyl ester mixture by the following method.

Firstly, 50 g of distilled water was added to 50 g of silver nitrate to be stirred/dissolved. 20 g of a mixture of fatty acid ethyl esters (acid value 0.2 to 1.5; POV 1.0 to 9.5; EPA ethyl ester purity 40-48% (fatty acid composition area %); DHA ethyl ester purity 5-10%) was mixed with 100 g of this silver nitrate aqueous solution, and stirring was performed for 30 minutes at 20° C. Subsequently, the solution was left to stand for 30 minutes, and was separated into two layers. This upper layer was disposed, and only the lower layer was separately collected for addition of 100 g of cyclohexane to be stirred for 30 minutes at 60° C. Subsequently, the solution was left to stand for 30 minutes, and was separated into two layers. This upper layer was separately collected to obtain a concentrate of highly unsaturated fatty acid ethyl esters. In addition, the lower layer containing silver nitrate was separately taken to measure the free fatty acid content. This lower layer containing silver nitrate was used for purification of highly unsaturated fatty acid ethyl esters again. The above-described reactions were carried out under nitrogen atmosphere. These operations were repeated.

Example 3 (Using Raw Materials where POV 15 of Raw Materials is Decreased to POV 1 with Activated Clay)

A highly unsaturated fatty acid ethyl ester was obtained from a fatty acid ethyl ester mixture by the following method.

Firstly, 10 g of activated clay was added to 1 kg of a mixture of fatty acid ethyl esters (acid value 0.5; POV 15; EPA ethyl ester purity 45.3% (fatty acid composition area %); DHA ethyl ester purity 6.8%) to be stirred for 30 minutes at 50° C. under nitrogen atmosphere. Subsequently, the activated clay was removed by filtering, and when POV was measured, it was 1.0. 20 g of this mixture of fatty acid ethyl esters (acid value 0.6; POV 1.0) was mixed with 100 g of a silver nitrate aqueous solution, where 50 g of distilled water was added to 50 g of silver nitrate to be stirred/dissolved, and stirring was performed for 30 minutes at 10° C. Subsequently, the solution was left to stand for 30 minutes, and was separated into two layers. This upper layer was disposed, and only the lower layer was separately collected for addition of 200 g of cyclohexane to be stirred for 30 minutes at 40° C. Subsequently, the solution was left to stand for 30 minutes, and was separated into two layers. This upper layer was separately collected to obtain a concentrate of highly unsaturated fatty acid ethyl esters. In addition, the lower layer containing silver nitrate was sepa-

TABLE 2

(Summary of results of Example 2) Using raw materials having various POVs and acid values

| | Fatty acid derivative | | | | Purified highly unsaturated fatty acid derivative | | | | |
|---|---|---|---|---|---|---|---|---|---|
| Batch number | peroxide value | acid value | EPA ethyl ester (%) | DHA ethyl ester (%) | peroxide value | acid value | yield (%) | EPA ethyl ester (%) | DHA ethyl ester (%) |
| 1 | 1.5 | 0.2 | 40.5 | 9.5 | 1.6 | 0.2 | 43.0 | 72.5 | 18.4 |
| 2 | | | | | 2.0 | 0.2 | 43.8 | 71.9 | 18.9 |
| 3 | | | | | 1.9 | 0.2 | 43.2 | 72.1 | 18.6 |
| 4 | 9.5 | 0.9 | 43.8 | 7.6 | 8.6 | 0.9 | 46.2 | 76.9 | 13.3 |
| 5 | | | | | 9.3 | 0.9 | 46.5 | 76.5 | 13.6 |
| 6 | | | | | 9.8 | 0.9 | 46.3 | 77.1 | 13.1 |
| 7 | 5.2 | 1.5 | 47.8 | 6.8 | 5.1 | 1.4 | 46.7 | 76.9 | 13.6 |
| 8 | | | | | 5.8 | 1.6 | 47.2 | 77.2 | 13.0 |
| 9 | | | | | 4.9 | 1.5 | 46.9 | 76.7 | 13.4 |
| 10 | | | | | 5.5 | 1.3 | 47.1 | 77.0 | 13.1 |

The results of treating 10 batches of the above-described mixture are shown in the above-described Table 2. These results show that the peroxide values do not correlate with the acid values, and that remarkable purity and yield could be obtained by setting the peroxide value to 10 or smaller.

rately taken to measure the free fatty acid content. This lower layer containing silver nitrate was used for purification of highly unsaturated fatty acid ethyl esters again. The above-described reactions were carried out under nitrogen atmosphere. These operations were repeated.

TABLE 3

(Summary of Results of Example 3) (Using raw materials where POV 15 of raw materials is decreased to POV 1 with activated clay)

| | Fatty acid derivative | | | | Purified highly unsaturated fatty acid derivative | | | | |
|---|---|---|---|---|---|---|---|---|---|
| Batch number | peroxide value | acid value | EPA ethyl ester (%) | DHA ethyl ester (%) | peroxide value | acid value | yield (%) | EPA ethyl ester (%) | DHA ethyl ester (%) |
| 1 | 1.0 | 0.6 | 45.3 | 6.8 | 1.1 | 0.6 | 47.1 | 77.0 | 12.9 |
| 2 | | | | | 0.9 | 0.6 | 46.9 | 77.2 | 12.6 |
| 3 | | | | | 1.3 | 0.7 | 46.8 | 77.1 | 12.9 |
| 4 | | | | | 1.0 | 0.6 | 47.0 | 76.9 | 13.1 |
| 5 | | | | | 1.6 | 0.7 | 47.2 | 77.1 | 13.0 |
| 6 | | | | | 1.3 | 0.6 | 46.9 | 77.3 | 12.6 |
| 7 | | | | | 1.1 | 0.7 | 47.3 | 77.5 | 12.4 |
| 8 | | | | | 1.2 | 0.7 | 46.8 | 77.1 | 12.8 |
| 9 | | | | | 1.3 | 0.6 | 46.9 | 76.9 | 13.1 |
| 10 | | | | | 0.9 | 0.6 | 47.2 | 77.2 | 12.8 |

The results of treating 10 batches of the above-described mixture are shown in the above-described Table 3. These results demonstrate that a remarkable effect was exerted by decreasing the peroxide value from 15 to 1.0.

Comparative Example 1 (Using Raw Materials with POV 15 Before the Decrease of POV in Example 3)

A highly unsaturated fatty acid ethyl ester was obtained from a fatty acid ethyl ester mixture by the following method.

20 g of a mixture of fatty acid ethyl esters (acid value 0.5; POV 15; EPA ethyl ester purity 45.3% (fatty acid composition area %); DHA ethyl ester purity 6.8%) was mixed with 100 g of a silver nitrate aqueous solution, where 50 g of distilled water was added to 50 g of silver nitrate to be stirred/dissolved, and stirring was performed for 60 minutes at 10° C. Subsequently, the solution was left to stand for 30 minutes, and was separated into two layers. This upper layer was disposed, and only the lower layer was separately collected for addition of 200 g of cyclohexane to be stirred for 30 minutes at 40° C. Subsequently, the solution was left to stand for 30 minutes, and was separated into two layers. This upper layer was separately collected to obtain a concentrate of highly unsaturated fatty acid ethyl esters. In addition, the lower layer containing silver nitrate was separately taken to measure the free fatty acid content. This lower layer containing silver nitrate was used for purification of highly unsaturated fatty acid ethyl esters again. The above-described reactions were carried out under nitrogen atmosphere. These operations were repeated.

TABLE 4

(Summary of results of Comparative Example 1) Using raw materials before the decrease of POV in Example 3

| | Fatty acid derivative | | | | Purified highly unsaturated fatty acid derivative | | | | |
|---|---|---|---|---|---|---|---|---|---|
| Batch number | peroxide value | acid value | EPA ethyl ester (%) | DHA ethyl ester (%) | peroxide value | acid value | yield (%) | EPA ethyl ester (%) | DHA ethyl ester (%) |
| 1 | 15.0 | 0.5 | 45.3 | 6.8 | 15.2 | 0.6 | 46.5 | 76.8 | 13.5 |
| 2 | | | | | 14.6 | 0.7 | 46.2 | 77.1 | 13.2 |
| 3 | | | | | 15.3 | 0.8 | 45.8 | 76.9 | 13.7 |
| 4 | | | | | 15.0 | 0.8 | 45.4 | 77.2 | 13.2 |
| 5 | | | | | 15.5 | 0.9 | 45.2 | 77.3 | 13.1 |
| 6 | | | | | 14.9 | 0.8 | 44.6 | 76.9 | 13.8 |
| 7 | | | | | 15.2 | 0.8 | 44.2 | 76.5 | 13.9 |
| 8 | | | | | 15.4 | 0.9 | 43.7 | 76.2 | 14.1 |
| 9 | | | | | 14.7 | 0.9 | 43.1 | 76.1 | 14.3 |
| 10 | | | | | 15.2 | 0.9 | 42.3 | 76.3 | 14.1 |

The results of treating 10 batches of the above-described mixture are shown in the above-described Table 4. When compared to the results of Table 3 (the case where the peroxide value is decreased from 15 to 1.0), the results of Table 4 demonstrate that a remarkable effect of the present invention was confirmed by decreasing the peroxide value from 15 to 1.0.

Comparative Example 2 (Conducted by Changing the Condition of Example 1, which is Under Nitrogen Atmosphere, to an Open Air System)

A highly unsaturated fatty acid ethyl ester was obtained from a fatty acid ethyl ester mixture by the following method.

Firstly, 50 g of distilled water was added to 50 g of silver nitrate to be stirred/dissolved. 20 g of a mixture of fatty acid ethyl esters (acid value 0.7; POV 6; EPA ethyl ester purity 44.9% (fatty acid composition area %); DHA ethyl ester purity 7.4%) was mixed with 100 g of this silver nitrate aqueous solution, and stirring was performed for 60 minutes at 20° C. Subsequently, the solution was left to stand for 60 minutes, and was separated into two layers. This upper layer was disposed, and only the lower layer was separately collected for addition of 100 g of cyclohexane to be stirred for 60 minutes at 60° C. Subsequently, the solution was left to stand for 30 minutes, and was separated into two layers. This upper layer was separately collected to obtain a concentrate of highly unsaturated fatty acid ethyl esters. In addition, the lower layer containing silver nitrate was separately taken to measure the free fatty acid content. This lower layer containing silver nitrate was used for purification of highly unsaturated fatty acid ethyl esters again. The above-described reactions were carried out in an open air system. These operations were repeated.

equivalent scope of technology, based on the description of the present invention and common knowledge from the description of the detailed preferred Embodiments of the present invention. Furthermore, it is understood that any patent, any patent application and any references cited in the present specification should be incorporated by reference in the present specification in the same manner as the contents are specifically described therein.

INDUSTRIAL APPLICABILITY

According to the present invention, a method of producing/purifying highly unsaturated fatty acids and/or derivatives thereof while suppressing deterioration of a silver salt aqueous solution is provided in production/purification of highly unsaturated fatty acids and/or derivatives thereof using the aqueous solution of silver salt.

The invention claimed is:

1. A method of purifying highly unsaturated fatty acid derivatives from a mixture comprising highly unsaturated fatty acid derivatives, comprising a step selected from the group consisting of the following (1) to (4):
   (1) (a) providing the mixture having a peroxide value (POV) of 1 or smaller, wherein the peroxide value of the mixture is adjusted by a POV reducing agent, and
   (b) contacting the mixture with an aqueous solution of silver salt;
   (2) (a) providing the mixture having a peroxide value of 1 or smaller, wherein the peroxide value of the mixture is adjusted by a POV reducing agent, and
   (b) mixing the mixture with an aqueous solution of silver salt;
   (3) (a) decreasing a peroxide value of the mixture to 1 or smaller by contacting the mixture with a POV reducing agent, and

TABLE 5

(Summary of results of Comparative example 2) Conducted by changing the condition of Example 1, which is under nitrogen atmosphere, to an open air system

| | Fatty acid derivative | | | | Purified highly unsaturated fatty acid derivative | | | | |
|---|---|---|---|---|---|---|---|---|---|
| Batch number | peroxide value | acid value | EPA ethyl ester (%) | DHA ethyl ester (%) | peroxide value | acid value | yield (%) | EPA ethyl ester (%) | DHA ethyl ester (%) |
| 1 | 6.0 | 0.7 | 44.9 | 7.4 | 12.3 | 0.6 | 46.5 | 77.0 | 12.9 |
| 2 | | | | | 19.5 | 0.7 | 46.0 | 77.2 | 12.6 |
| 3 | | | | | 20.1 | 0.6 | 45.7 | 77.1 | 12.9 |
| 4 | | | | | 22.3 | 0.7 | 45.2 | 76.9 | 13.1 |
| 5 | | | | | 16.4 | 0.8 | 44.9 | 77.1 | 13.0 |
| 6 | | | | | 20.1 | 0.7 | 44.2 | 77.3 | 12.6 |
| 7 | | | | | 19.6 | 0.7 | 43.9 | 77.5 | 12.4 |
| 8 | | | | | 22.1 | 0.7 | 43.1 | 77.1 | 12.8 |
| 9 | | | | | 20.3 | 0.8 | 42.7 | 76.9 | 13.1 |
| 10 | | | | | 18.5 | 0.8 | 42.1 | 77.2 | 12.8 |

The results of treating 10 batches of the above-described mixture are shown in the above-described Table 5. When these results are compared to the results of Example 1, it is demonstrated that the results under nitrogen atmosphere exert a more remarkable effect than the case of the open air system.

As described above, the present invention is exemplified by the use of its preferred Embodiments of the present invention. However, the present invention should not be interpreted solely based on the Embodiments. It is understood that the scope of the present invention should be interpreted solely based on the scope of the claims. It is also understood that those skilled in the art can implement (b) contacting the mixture with an aqueous solution of silver salt; and
(4) (a) decreasing a peroxide value of the mixture to 1 or smaller by contacting the mixture with a POV reducing agent, and
(b) mixing the mixture with an aqueous solution of silver salt,
wherein the derivatives comprise at least one of a methyl ester, ethyl ester, amide, methyl amide, triglyceride, diglyceride or monoglyceride derivative.

2. The method according to claim 1, wherein the highly unsaturated fatty acid derivatives are highly unsaturated fatty acid ethyl esters.

3. The method according to claim 2, wherein the highly unsaturated fatty acid ethyl esters are selected from the group consisting of 18:3ω3, 18:3ω6, 18:4ω3, 20:4ω6, 20:5ω3, 22:5ω3, and 22:6ω3.

4. The method according to claim 1, wherein the aqueous solution of silver salt is a silver nitrate aqueous solution.

5. The method of claim 1, wherein the POV reducing agent is selected from the group consisting of acid clay, activated clay, activated carbon, and silicic acid.

6. The method according to claim 1, further comprising (c) adding an antioxidant to the mixture.

7. The method according to claim 6, wherein the step (c) is performed before the step (b).

8. The method according to claim 1, wherein the step (b) is performed under a condition selected from the group consisting of under a nitrogen gas environment and under a light-blocking environment.

* * * * *